United States Patent
James et al.

(10) Patent No.: US 8,024,038 B2
(45) Date of Patent: Sep. 20, 2011

(54) IMPLANTABLE DEVICE WITH VOLTAGE DELAY TEST

(75) Inventors: Kristofer J. James, Eagan, MN (US); Hal M. Propp, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 237 days.

(21) Appl. No.: 12/340,692

(22) Filed: Dec. 20, 2008

(65) Prior Publication Data

US 2009/0171409 A1 Jul. 2, 2009

Related U.S. Application Data

(60) Provisional application No. 61/009,748, filed on Dec. 30, 2007.

(51) Int. Cl.
*A61N 1/00* (2006.01)
(52) U.S. Cl. .............................................. 607/5; 607/29
(58) Field of Classification Search ................. 607/4–14, 607/27–29
See application file for complete search history.

(56) References Cited

U.S. PATENT DOCUMENTS

| | | | |
|---|---|---|---|
| 5,507,786 A | 4/1996 | Morgan et al. | |
| 5,741,307 A | 4/1998 | Kroll | |
| 5,769,873 A | 6/1998 | Zadech | |
| 5,925,068 A | 7/1999 | Kroll | |
| 5,959,371 A * | 9/1999 | Dooley et al. | 307/130 |
| 6,129,746 A | 10/2000 | Levine et al. | |
| 6,366,812 B1 | 4/2002 | Levine et al. | |
| 6,426,628 B1 * | 7/2002 | Palm et al. | 324/427 |
| 6,490,484 B2 | 12/2002 | Dooley et al. | |
| 6,826,427 B1 * | 11/2004 | Fayram et al. | 607/29 |
| 7,024,246 B2 | 4/2006 | Acosta et al. | |
| 7,026,791 B2 * | 4/2006 | Palazzo et al. | 320/129 |
| 7,058,451 B2 | 6/2006 | Obel et al. | |
| 7,167,756 B1 | 1/2007 | Torgerson et al. | |
| 7,239,146 B2 | 7/2007 | James et al. | |
| 7,248,920 B2 * | 7/2007 | Norton et al. | 607/5 |
| 7,375,496 B2 * | 5/2008 | Gan et al. | 320/132 |
| 2008/0097544 A1 | 4/2008 | Gandhi et al. | |
| 2009/0182517 A1 | 7/2009 | Gandhi et al. | |

* cited by examiner

*Primary Examiner* — Niketa I Patel
*Assistant Examiner* — Catherine Voorhees
(74) *Attorney, Agent, or Firm* — Schwegman, Lundberg & Woessner, P.A.

(57) ABSTRACT

An implantable medical device (IMD), such as a defibrillator, performs a capacitor reform or other temporary high current mode, such as to maintain efficacy of a battery or a high voltage defibrillation energy storage capacitor in spite of non-use. Before performing the capacitor reform or other high current mode, a voltage delay test can be performed. A voltage delay can be declared when an initial battery voltage measurement is less than a later battery voltage measurement during a loaded condition such as the charging of the capacitor. If a voltage delay is present, the capacitor reform or other temporary high current mode is enabled, otherwise, the capacitor reform or other temporary high current mode is inhibited. This saves energy, increasing the life of the IMD before explant.

18 Claims, 3 Drawing Sheets

IMPLANTABLE DEVICE WITH VOLTAGE DELAY TEST

CLAIM OF PRIORITY

This non-provisional application claims the benefit of priority under 35 U.S.C. §119(e) to U.S. Provisional Patent Application Ser. No. 61/009,748, filed Dec. 30, 2007, the specification of which is herein incorporated by reference in its entirety.

TECHNICAL FIELD

This document pertains generally to implantable medical devices, and more particularly, but not by way of limitation, to an implantable medical device with a voltage delay test.

BACKGROUND

Implantable medical devices (IMDs) can include implantable cardioverters or defibrillators, which can monitor for an arrhythmia and can deliver a high voltage shock to interrupt a fibrillating or tachyarrhythmic heart. This provides an opportunity for a normal heart rhythm to resume.

The high energy for the defibrillation or cardioversion shock can be generated in the IMD by using a flyback or other DC-to-DC voltage converter to upconvert a relatively low battery voltage (e.g., 3-6 Volts) to a high voltage (e.g., 300-800 Volts). The high voltage can be stored on a high voltage capacitor until shock delivery is desired. Then, a switch can be closed to deliver the defibrillation/cardioversion energy from the high voltage capacitor to electrodes located as desired in association with the subject to be defibrillated.

OVERVIEW

An implantable medical device (IMD), such as a defibrillator, performs a capacitor reform or other temporary high current mode, such as to maintain efficacy of a battery or a high voltage defibrillation energy storage capacitor in spite of non-use. Before performing the capacitor reform or other high current mode, a voltage delay test can be performed. A voltage delay can be declared when an initial battery voltage measurement is less than a later battery voltage measurement during a loaded condition such as the charging of the capacitor. If a voltage delay is present, the capacitor reform or other temporary high current mode is enabled, otherwise, the capacitor reform or other temporary high current mode is inhibited. This saves energy, increasing the life of the IMD before explant.

Example 1 describes an implantable apparatus. In this example, the implantable apparatus can comprise a battery. A high voltage storage capacitor can be configured for storing at least one of defibrillation energy and cardioversion energy. A high voltage storage capacitor charging circuit can be coupled to the battery and the high voltage capacitor. A battery voltage measurement circuit can be coupled to the battery. A processor can be coupled to battery voltage measurement circuit. The processor can be configured to recurrently test for a battery voltage delay, to enable a temporary mode that draws high current from the battery when the battery voltage delay is present, and to inhibit the temporary high current mode when the battery voltage delay is absent.

In Example 2, the apparatus of Example 1 can optionally be configured such that the processor can enable reforming of the high voltage storage capacitor when the battery voltage delay is present.

In Example 3, the apparatus of any one or more of Examples 1-2 can optionally be configured such that the processor is configured to initiate the test for the battery voltage delay upon completion of a time duration timed by the processor.

In Example 4, the apparatus of any one or more of Examples 1-3 can optionally be configured to include a detection circuit configured to detect a triggering event. The processor can be configured to determine when a triggering event is present, and to initiate the test for the battery voltage delay in response to the triggering event.

In Example 5, the apparatus of any one or more of Examples 1-4 can optionally be configured such that the detection circuit includes an arrhythmia detection circuit and wherein the triggering event includes initiation of charging of a high voltage capacitor 5 in response to a detected arrhythmia.

In Example 6, the apparatus of any one or more of Examples 1-5 can optionally be configured such that the processor is configured to initiate the test for the battery voltage delay after a first time duration in the absence of a triggering event during the first time duration, to initiate timing of a second different time duration after testing for the battery voltage delay in response to a triggering event, and to initiate the test for the battery voltage delay after the second time duration in the absence of a triggering event during the second time duration.

In Example 7, the apparatus of any one or more of Examples 1-6 can optionally be configured such that the processor is configured to initiate the temporary high current mode to test for the battery voltage delay, and to substantially immediately discontinue the temporary high current mode when the battery voltage delay is absent.

In Example 8, the apparatus of any one or more of Examples 1-7 can optionally be configured such that the high voltage storage capacitor charging circuit includes a switched mode DC-to-DC converter circuit.

Example 9 describes a method. In this example, the method can comprise: recurrently testing for a battery voltage delay in an implantable medical device (IMD) having at least one of cardioversion capability and defibrillation capability; temporarily entering an IMD mode that draws high current from the battery when the battery voltage delay is detected by the testing; and inhibiting the temporary high current mode when the battery voltage delay is absent in the testing.

In Example 10, the method of Example 9 can optionally be performed such that entering the temporary high current mode includes performing capacitor reform.

In Example 11, the method of any one or more of Examples 9-10 can optionally be performed such that recurrently testing for battery voltage delay includes testing for the battery voltage delay upon expiration of a timer in the IMD.

In Example 12, the method of any one or more of Examples 9-11 can optionally be performed such that recurrently testing for battery voltage delay includes testing for the battery voltage delay when the IMD detects a triggering event.

In Example 13, the method of any one or more of Examples 9-12 can optionally be performed such that testing for battery voltage delay in response to the triggering event includes testing for battery voltage delay when initiating charging of a high voltage capacitor.

In Example 14, the method of any one or more of Examples 9-13 can optionally be performed such that recurrently testing for battery voltage delay includes: testing for the battery voltage delay when a triggering event is absent during a first time duration; initiating timing of a second different time duration after testing for the battery voltage delay in response to a triggering event; and testing for the battery voltage delay when a triggering event is absent during the second time duration.

In Example 15, the method of any one or more of Examples 9-14 can optionally be performed such that testing for the battery voltage delay includes initiating the temporary high current mode, and wherein inhibiting the temporary high current mode includes substantially immediately discontinuing the temporary high current mode when the battery voltage delay is absent.

Example 16 describes a machine readable medium including instructions that, when performed by a machine, result in the machine: recurrently testing for a battery voltage delay in an IMD having at least one of cardioversion capability and defibrillation capability; enabling a temporary mode that draws high current from an IMD battery when the battery voltage delay is detected by the testing; and inhibiting the temporary high current mode when the battery voltage delay is absent in the testing.

In Example 17, the machine readable medium of Example 16 can optionally include instructions that, when performed by the machine, result in the machine testing for the battery voltage delay upon expiration of a timer in the IMD.

In Example 18, the machine readable medium of any one or more of Examples 16-17 can optionally include instructions that, when performed by the machine, result in the machine testing for the battery voltage delay when the IMD detects a triggering event.

In Example 19, the machine readable medium of any one or more of Examples 16-18 can optionally include instructions that, when performed by the machine, result in the machine: testing for the battery voltage delay when a triggering event is absent during a first time duration; initiating timing of a second different time duration after testing for the battery voltage delay in response to a triggering event; and testing for the battery voltage delay when a triggering event is absent during the second time duration.

In Example 20, the machine readable medium of any one or more of Examples 16-18 can optionally include instructions that, when performed by the machine, result in the machine: initiating the temporary high current mode to test for the battery voltage delay; and substantially immediately discontinuing the temporary high current mode when the battery voltage delay is absent.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
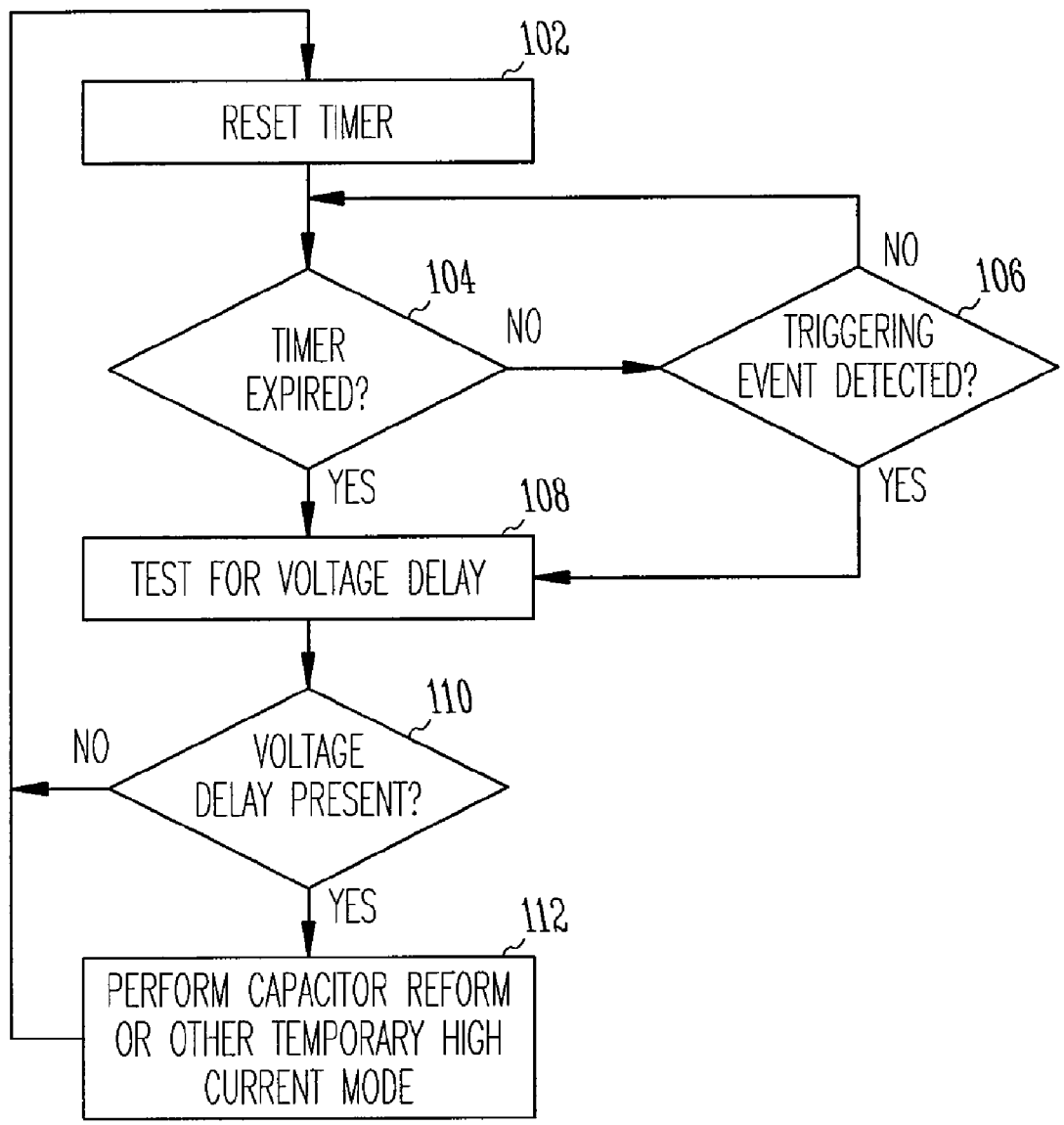
FIG. 1 is an illustrative example of a method of testing whether a voltage delay is present, such as to determine whether to perform a capacitor reform.

The present inventors have recognized that certain high voltage capacitors for storing the defibrillation energy can lose their effectiveness during an extended period of non-use. As an illustrative (but non-limiting) example, suppose that an aluminum electrolytic capacitor is used as the high voltage capacitor for storing the defibrillation energy. This type of capacitor can include strips of aluminum foil and electrolyte-impregnated paper. Each strip of aluminum foil can be covered with an aluminum oxide, which insulates the foils from the electrolyte in the paper. One maintenance issue with aluminum electrolytic capacitors concerns the degradation of their charging efficiency after long periods of inactivity. The degraded charging efficiency, which is believed to stem from instability of the aluminum oxide in the liquid electrolyte, ultimately requires the battery to progressively expend more and more energy to charge the capacitors for providing therapy.

Thus, to repair this degradation, a processor in the IMD can be programmed to regularly charge and hold aluminum electrolytic capacitors at or near a maximum-energy voltage (the voltage corresponding to maximum energy) for a time period less than one minute, before discharging them internally through a non-therapeutic load. (In some cases, the maximum-energy voltage is allowed to leak off slowly rather than being maintained; in others, it is allowed to leak off (or droop) for 60 seconds and discharged through a non-therapeutic load; and in still other cases, the voltage is alternately held for five seconds and drooped for 10 seconds over a total period of 30 seconds, before being discharged through a non-therapeutic load.) These periodic charge-hold-discharge (or charge-hold-droop-discharge) cycles for capacitor maintenance are called capacitor "reforms." Wet-tantalum capacitors may similarly exhibit degradation from disuse and, therefore, may also benefit from capacitor reform. Certain batteries may also exhibit degradation from disuse at a high current draw, which may result in formation of an oxidation or other layer about the battery anode, thereby increasing the apparent battery impedance of the battery. Therefore, such batteries may also benefit from the same capacitor reform, or any other recurrent mode that tends to draw a high current from the battery, thereby disrupting the resistive layer formed about the battery anode. Unfortunately, the capacitor reform (or other high current draw mode) expends energy and, therefore, tends to reduce battery life of the IMD, thereby hastening its explantation and replacement.

The present inventors have recognized, among other things, that it is possible to test whether a capacitor reform or (other temporary high current mode) is actually needed. By performing capacitor reform or other high current mode only when actually needed, the energy used in performing the capacitor reform or high current mode can be saved. This can increase the battery life of the IMD, thereby prolonging its useful life before explantation and replacement occurs.

FIG. 1 is an illustrative example of a method of testing whether a voltage delay is present, such as to determine whether to perform a capacitor reform or high current mode. At 102, one or more timers are reset. At 104 and 106, monitoring is concurrently performed for expiration of the timer or detection of a test-triggering event. One example of a triggering event is the occurrence of a capacitor charging, such as for a defibrillation shock delivery. At 104, if the timer expires, then a voltage delay test is performed at 108, otherwise triggering event detection is checked at 106. If a triggering event is detected at 106, process flow proceeds to 108 to test for voltage delay during the charging for defibrillation shock delivery, otherwise process flow returns to 104 to wait for the timer to expire. Voltage delay refers to a time delay for the voltage of the battery to reach a maximum after a device mode is enabled that involves a high current drain from the battery (e.g., charging of a high voltage capacitor). The voltage delay test is described below in regard to FIGS. 3A-3B.

If desired, a different timer period can be used depending on whether a triggering event was detected at 106, or whether the timer expired at 104 without having detected such a triggering event at 106. For example, a high voltage capacitor charging in preparation for a defibrillation shock delivery may trigger a different timer duration than a previous voltage delay measurement that did not result in performing a capacitor reform, as discussed below.

At 110, after testing for voltage delay at 108, if a voltage delay is present, a capacitor reform (or other temporary high current mode) is performed at 112 and the timer is then reset at 102, otherwise, the capacitor reform or other high current mode at 112 is skipped and the timer is reset at 102. Process flow then repeats, such as described above. Typically, a high current mode can draw about one amp (1 A) of current from the battery. For example, charging of a high voltage capacitor can draw from one to three amps from the battery.

Figure 2:
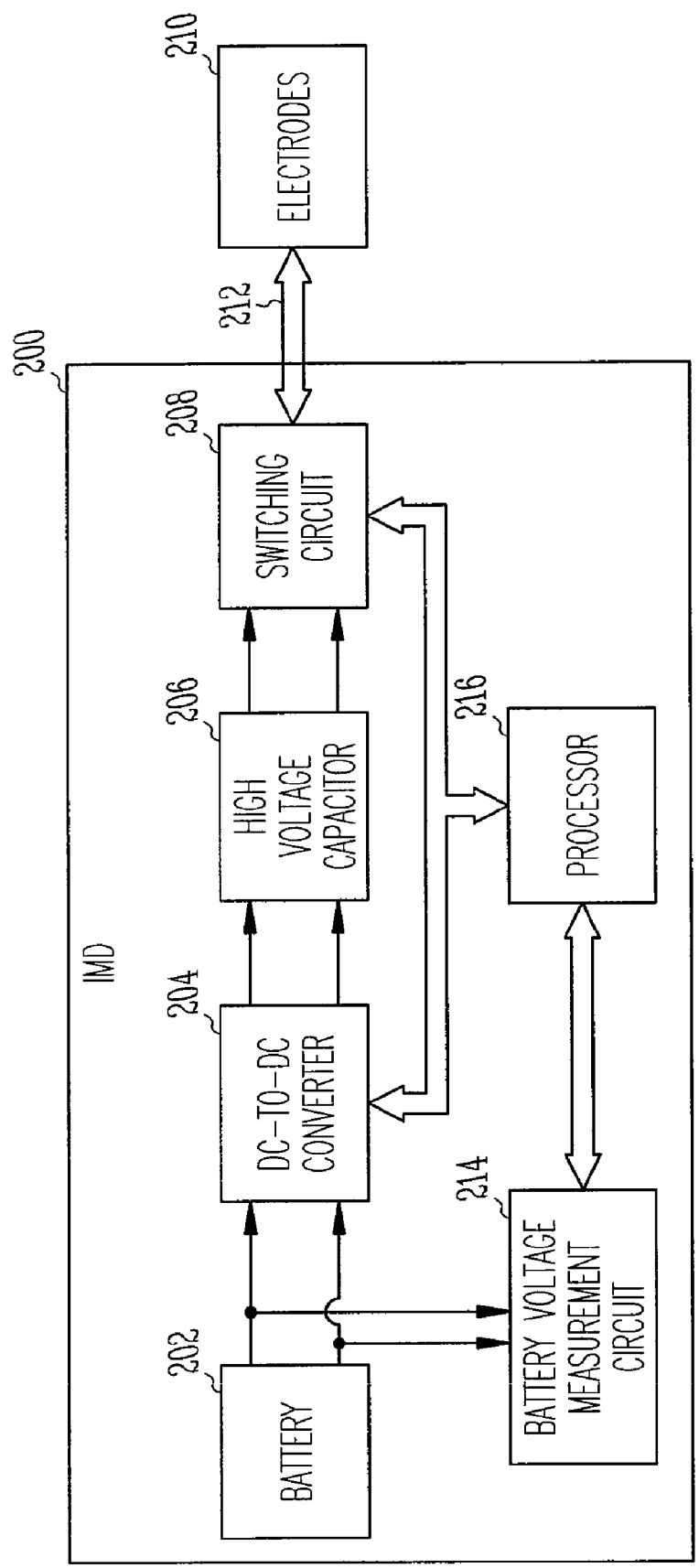
FIG. 2 is a block diagram of an IMD 200 including certain portions that may be germane to the present discussion of testing for voltage delay and performing a capacitor reform.

FIG. 2 is a block diagram of an IMD 200 including certain portions that may be germane to the present discussion of testing for voltage delay and performing a capacitor reform or other temporary high current mode. In this example, the IMD 200 includes a battery 202, which is coupled to at least one high voltage capacitor 206 by a switched-mode or other DC-to-DC converter circuit 204. A switching circuit 208 selectively couples the high voltage capacitor 206 to desired electrodes 210, located in association with the subject to be defibrillated, such as via one or more leads 212 or other conductors. A battery measurement circuit 214 is configured to measure the terminal voltage of the battery 202, such as during charging of the high voltage capacitor 206 by the DC-to-DC converter 204. A processor 216 controls operation of, among other things, the DC-to-DC converter 204 and the switching circuit 208, such as to test for voltage delay or perform the capacitor reform or other temporary high current mode, such as described above with respect to FIG. 1. The processor 216 may include a digital signal processor, application specific integrated circuit (ASIC), microprocessor, or other type of processor, interpreting or executing instructions in software or firmware.

Figure 3A:
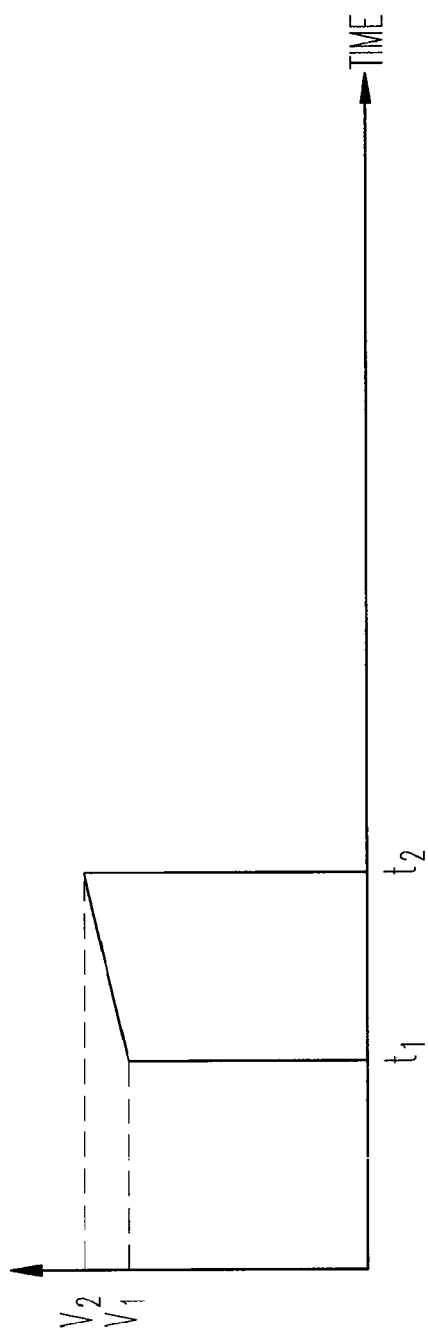
FIGS. 3A and 3B are graphs of voltage vs. time illustrating generally a first example in which voltage delay is present (FIG. 3A) and a second example in which voltage delay is absent (FIG. 3B).
Figure 3B:
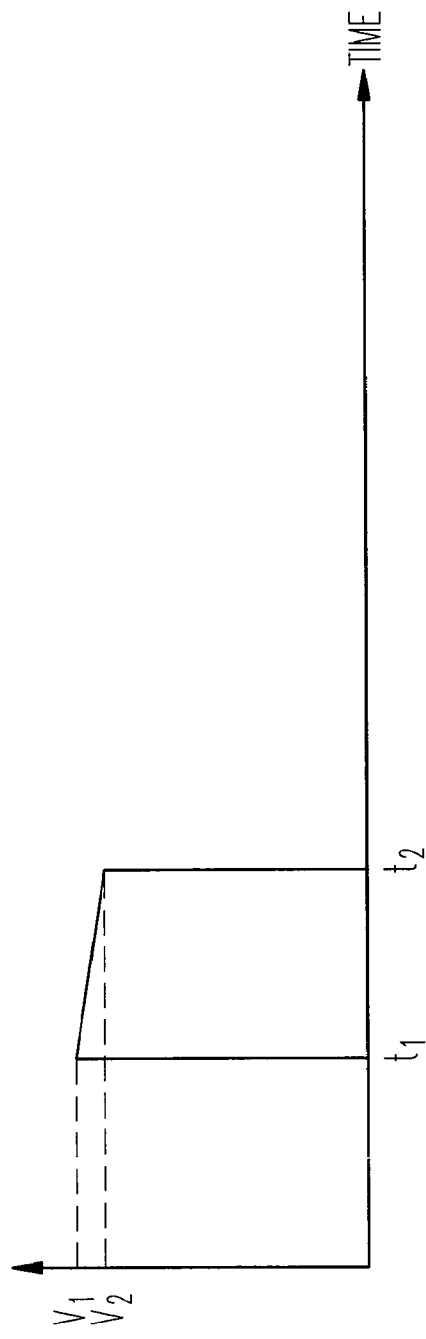

FIGS. 3A and 3B are graphs of voltage vs. time illustrating generally a first example in which voltage delay is present (FIG. 3A) and a second example in which voltage delay is absent (FIG. 3B). In certain examples, a voltage delay measurement is performed by initiating charging of the high voltage capacitor 206 by the DC-to-DC converter 204 shortly before (e.g., 100 ms) performing an initial battery terminal voltage measurement $v_1$ at time $t_1$. After a programmable time delay ($t_2-t_1$) (e.g., 2 seconds), a second battery terminal voltage measurement $v_2$ is performed at time $t_2$. If $v_2 > v_1$ (as shown in FIG. 3A), then a voltage delay condition is declared to exist, otherwise $v_2 \leq v_1$ (as shown in FIG. 3B), and a voltage delay condition is declared absent.

If the voltage delay condition is absent, then charging of the high voltage capacitor is discontinued immediately, thereby conserving any further energy that would have been used in further charging the high voltage capacitor, such as in performing a full capacitor reform.

If the voltage delay condition exists, then a capacitor reform (or other temporary high current mode) is performed, such as by continuing to charge the high voltage capacitor to a specified high voltage value (e.g., 750 Volts) such as that stored for usage in delivering a defibrillation shock.

In an example in which the voltage delay measurement is performed with a similar regularity as capacitor reform would otherwise be performed (e.g., without such voltage delay measurement), then by comparison, using the voltage delay measurement to decide whether to perform the capacitor reform will save energy in the instances in which no voltage delay is present. This can increase the battery life of the IMD, thereby prolonging its useful life before explantation and replacement occurs.

In an example, a voltage delay measurement is also performed when the IMD monitoring (e.g., detection circuit 218) detects an arrhythmia and responds by charging the high voltage capacitor in preparation for delivering a defibrillation shock. If this charging continues (e.g., is not aborted) beyond time $t_2$, then the battery voltage measurements can be obtained for testing for any voltage delay. If no voltage delay is present, then the timer can be reset, thereby putting off the next voltage delay test and delaying expenditure of the energy associated therewith.

Although specific examples have been given for the values associated with the times $t_1$, $t_2$, etc., in certain examples, such values are programmable, such as by the designer, an end-user, or as a function of another automated process of the IMD.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable apparatus comprising:
a battery;
a high voltage storage capacitor for storing at least one of defibrillation energy and cardioversion energy;
a high voltage storage capacitor charging circuit, coupled to the battery and the high voltage capacitor;
a battery voltage measurement circuit, coupled to the battery; and
a processor, coupled to battery voltage measurement circuit, configured to:
recurrently test for a battery voltage delay via initiating a temporary high current mode that draws high current from the battery to determine the presence or absence of the battery voltage delay;
continue the temporary high current mode when determining that the battery voltage delay is present; and
substantially immediately discontinue the temporary high current mode when the battery voltage delay is absent.

2. The apparatus of claim 1, wherein the processor is configured to enable reforming of the high voltage storage capacitor when the battery voltage delay is present.

3. The apparatus of claim 1, wherein the processor is configured to initiate the test for the battery voltage delay upon completion of a time duration timed by the processor.

4. The apparatus of claim 1, including a detection circuit configured to detect a triggering event, and wherein the processor is configured to:
determine when a triggering event is present; and
initiate the test for the battery voltage delay in response to the triggering event.

5. The apparatus of claim 4, wherein the detection circuit includes an arrhythmia detection circuit and wherein the triggering event includes initiation of charging of a high voltage capacitor in response to a detected arrhythmia.

6. The apparatus of claim 1, wherein the high voltage storage capacitor charging circuit includes a switched mode DC-to-DC converter circuit.

7. The implantable apparatus of claim 1, wherein the processor is configured to enable a temporary mode that draws high current from the battery when determining the battery voltage delay is present by detecting an increase in battery voltage during charging of the high voltage storage capacitor.

8. An implantable apparatus comprising:
a battery;
a high voltage storage capacitor for storing at least one of defibrillation energy and cardioversion energy;
a high voltage storage capacitor charging circuit, coupled to the battery and the high voltage capacitor;
a battery voltage measurement circuit, coupled to the battery; and
a detection circuit configured to detect a triggering event;
a processor, coupled to battery voltage measurement circuit, wherein the processor is configured to:
recurrently test for a battery voltage delay, including:
initiate the test for the battery voltage delay after a first time duration in the absence of the triggering event during the first time duration;
initiate timing of a second different time duration after testing for the battery voltage delay in response to the triggering event; and
initiate the test for the battery voltage delay after the second time duration in the absence of the triggering event during the second time duration;
enable a temporary mode that draws high current from the battery when the battery voltage delay is present; and
inhibit the temporary high current mode when the battery voltage delay is absent.

9. A method comprising:
recurrently testing for a battery voltage delay in an implantable medical device (IMD) having at least one of cardioversion capability and defibrillation capability, wherein testing for the battery voltage delay includes; initiating a temporary IMD mode that draws high current from the battery when the battery voltage delay is detected by the testing; and
substantially immediately discontinuing the temporary high current mode when the battery voltage delay is absent in the testing.

10. The method of claim 9, wherein entering the temporary high current mode includes performing capacitor reform.

11. The method of claim 9, wherein recurrently testing for battery voltage delay includes testing for the battery voltage delay upon expiration of a timer in the IMD.

12. The method of claim 9, including:
detecting a triggering event with the IMD that triggers a test for a battery voltage delay, and
wherein recurrently testing for battery voltage delay includes testing for the battery voltage delay when the IMD detects the triggering event.

13. The method of claim 12, wherein testing for battery voltage delay in response to the triggering event includes testing for battery voltage delay when initiating charging of a high voltage capacitor.

14. A method comprising:
recurrently testing for a battery voltage delay in an implantable medical device (IMD) having at least one of cardioversion capability and defibrillation capability, including:
determining whether a triggering event is detected or absent;

testing for the battery voltage delay when the triggering event is absent during a first time duration;

initiating timing of a second different time duration after testing for the battery voltage delay in response to the triggering event; and testing for the battery voltage delay when the triggering event is absent during the second time duration;

temporarily entering an IMD mode that draws high current from the battery when the battery voltage delay is detected by the testing; and inhibiting the temporary high current mode when the battery voltage delay is absent in the testing.

15. A non-transitory machine readable medium including instructions that, when performed by a machine, result in the machine:

recurrently testing for a battery voltage delay via initiating a temporary high current mode in an implantable medical device (IMD) having at least one of cardioversion capability and defibrillation capability, wherein testing for the battery voltage delay includes testing for an increase in battery voltage;

determining whether the battery voltage delay is detected or absent during the testing;

continuing the temporary high current mode when the battery voltage delay is detected by the testing; and substantially immediately discontinuing the temporary high current mode when the battery voltage delay is absent in the testing.

16. The non-transitory machine readable medium of claim 15, including instructions that, when performed by the machine, result in the machine testing for the battery voltage delay upon expiration of a timer in the IMD.

17. The non-transitory machine readable medium of claim 15, including instructions that, when performed by the machine, result in the machine testing for the battery voltage delay when the IMD detects a triggering event.

18. A non-transitory machine readable medium including instructions that, when performed by a machine, result in the machine:

recurrently testing for a battery voltage delay in an implantable medical device (IMD) having at least one of cardioversion capability and defibrillation capability, wherein testing for the battery voltage delay includes:

determining whether a triggering event is detected or absent;

testing for the battery voltage delay when the triggering event is absent during a first time duration;

initiating timing of a second different time duration after testing for the battery voltage delay in response to the triggering event; and testing for the battery voltage delay when the triggering event is absent during the second time duration;

enabling a temporary mode that draws high current from an IMD battery when the battery voltage delay is detected by the testing; and inhibiting the temporary high current mode when the battery voltage delay is absent in the testing.

* * * * *

UNITED STATES PATENT AND TRADEMARK OFFICE
CERTIFICATE OF CORRECTION

PATENT NO.        : 8,024,038 B2
APPLICATION NO.   : 12/340692
DATED             : September 20, 2011
INVENTOR(S)       : Kristofer J. James et al.

Page 1 of 1

It is certified that error appears in the above-identified patent and that said Letters Patent is hereby corrected as shown below:

IN THE CLAIMS:
In column 8, line 39, in Claim 9, delete "includes;" and insert -- includes --, therefor.

Signed and Sealed this
Twenty-second Day of November, 2011

David J. Kappos
*Director of the United States Patent and Trademark Office*